US010945925B2

(12) United States Patent
Patel et al.

(10) Patent No.: US 10,945,925 B2
(45) Date of Patent: Mar. 16, 2021

(54) SMART BOTTLE USED FOR STORING LIQUIDS AND MEDICATIONS AND A METHOD FOR REMINDING TIMELY INTAKE THEREOF

(71) Applicants: Miteshkumar Ishwarbhai Patel, Sacramento, CA (US); Raj Kalpesh Patel, Ahmedabad (IN); Rihen Shah, Ahmedabad (IN); Sweet Swagatika, Ahmedabad (IN); Yash Nebhwani, Ahmedabad (IN); Amit Shakya, Ahmedabad (IN)

(72) Inventors: Miteshkumar Ishwarbhai Patel, Sacramento, CA (US); Raj Kalpesh Patel, Ahmedabad (IN); Rihen Shah, Ahmedabad (IN); Sweet Swagatika, Ahmedabad (IN); Yash Nebhwani, Ahmedabad (IN); Amit Shakya, Ahmedabad (IN)

(73) Assignee: Dosepack LLC

( * ) Notice: Subject to any disclaimer, the term of this patent is extended or adjusted under 35 U.S.C. 154(b) by 0 days.

(21) Appl. No.: 16/438,467

(22) Filed: Jun. 12, 2019

(65) Prior Publication Data
US 2020/0390655 A1  Dec. 17, 2020

(51) Int. Cl.
*A61J 7/04* (2006.01)
*A61J 1/14* (2006.01)
(Continued)

(52) U.S. Cl.
CPC .......... *A61J 7/0418* (2015.05); *A61J 1/1412* (2013.01); *A61J 7/0481* (2013.01); *G08B 21/18* (2013.01);
(Continued)

(58) Field of Classification Search
CPC .......... A61J 7/0046; A61J 7/04; A61J 7/0418; A61J 7/0436; A61J 7/0454; A61J 7/0481;
(Continued)

(56) References Cited

U.S. PATENT DOCUMENTS

| 2008/0296181 | A1* | 12/2008 | Stephens | ................ | A47G 23/16 206/217 |
| 2011/0169635 | A1* | 7/2011 | Johnson | ................ | G08B 21/24 340/540 |

(Continued)

*Primary Examiner* — Brian Wilson
(74) *Attorney, Agent, or Firm* — Creso Legal (57) ABSTRACT

A smart bottle used for storing liquids and medications is disclosed. The smart bottle includes electronics, memory, and a processor that causes alarms and reminders for user to take their medications in a timely manner.
The bottle shaped smart bottle is essentially an electronic device with liquid and medication storage compartments. It includes speaker for providing audible alerts to the users as well as their caregivers. It also includes a microphone that can be used by the user or caregiver to provide instructions relating to the intake of medication or to assist patients that have hand or finger arthritis.
The bottle has a longitudinal and circular body with a cap that can be twisted on/off at its top. The top, or the cap, is a smart cap that carries core intelligence and electronics. It comprises a microprocessor, in-built real-time clock, speaker and lights for intuitive alarms and microphone to hear the voice of user for ease of use.
The microprocessor is communicatively coupled through an electronic circuit to a plurality of electronic components housed within the smart bottle. These include alarms, microphone, displays, transmitter for sending out information, and an antenna for wireless connectivity.
The longitudinal main body of the smart bottle is circular in shape and includes a chamber for storing liquids, such as
(Continued)

water or other liquid. It also has compartments on its front and back side for storing a plurality of pills and medications. The smart bottle is wirelessly connected to a server. It has the capability of connecting to a patient database to obtain all patient related information as well as medication information and hours of administration information. The smart bottle fetches prescription data automatically when linked to Pharmacy. At the time of intake for a pill, the smart bottle reminds user for respective dosages through use of lights or audio alarms. The smart bottle also sends alerts to a caregiver and stored adherence and compliance data to a server. To do so, the smart bottle uses the transmitter to send alerts to mobile phone for reminding the user to take the medication or to send an alert to a caregiver.

The smart bottle also includes GSM and GPS modules. GPS mode allows the smart bottle to be located based on a GPS search. The GSM feature allows the user to make and receive calls from the smart bottle.

One method of operating the features of the smart bottle is through maneuvering and selecting preferences in a mobile application that is communicatively connected to the smart bottle. Another method of operating the features of the smart bottle is by having the user speak into the microphone and providing instructions. The instructions being processed through a voice activation module that is communicatively connected to the processor for operating the features. These features include dialing a phone number, setting an alert, and asking for medication details.

19 Claims, 10 Drawing Sheets

(51) Int. Cl.
*G08B 21/18* (2006.01)
*G16H 20/13* (2018.01)
(52) U.S. Cl.
CPC ........ *A61J 2200/30* (2013.01); *A61J 2200/76* (2013.01); *G16H 20/13* (2018.01)
(58) Field of Classification Search
CPC .. A61J 1/1412; A61J 1/14128; A61J 2200/30; A61J 2200/76; G16H 20/13
See application file for complete search history.

(56) References Cited

U.S. PATENT DOCUMENTS

| | | | |
|---|---|---|---|
| 2014/0262918 A1* | 9/2014 | Chu | A61J 1/03 206/534 |
| 2016/0286993 A1* | 10/2016 | Pau | A47G 23/16 |
| 2017/0176238 A1* | 6/2017 | Dubey | G01G 17/04 |

* cited by examiner

SMART BOTTLE USED FOR STORING LIQUIDS AND MEDICATIONS AND A METHOD FOR REMINDING TIMELY INTAKE THEREOF

FIELD OF THE INVENTION

The present invention relates generally to a smart bottle for storing medications, pills, and liquids, and electronic reminders and management associated with such containers for taking medication on time. More specifically, the present invention relates to a water bottle shaped container that includes on-board electronic devices, processor, and memory for electronically reminding the timely intake of medication and provides the convenience of storing liquids that are preferred to consume along with intake of the medication.

DISCUSSION OF THE RELATED ART

It is common for patients to forget to take their daily dosages of pills. It is also inconvenient for patients, specially the elderly or sick, to have to go and get water or other liquid for consuming the medication. Often, they are either not in a position to get the water, or have to rely on someone to get them the water. This becomes especially difficult at night time.

Many patients do not adherence to their intake schedule of medication that is guided by the Hours of Administration (HOA) provided by their physician. Non-Adherence is becoming and continues to be a very serious problem. The lower levels of compliance by the patient also result in the efficacy of the drug or the treatment of the disease of ailing condition not being properly addressed.

Non-compliance or non-adherence can be caused due to forgetfulness, misplacing the pills, taking the wrong pills, or patient not having water or other liquid nearby to consume the medication. In some instances, where patients have dementia or Alzheimer's, they would need reminders to take their medications.

To address the forgetfulness problem, there have been a few attempts made previously. These attempts have been made to remind the patients to take their medications on time. A few such attempts are described below. It is noted that although some attempts by others are described here, we do not admit that any of them qualify as prior art to our invention.

These include an automated dosage reminder device such as that disclosed in US Patent U.S. Pat. No. 8,174,370B1. This device has its own issues. To name a few, it is bulky and not portable. Yet another problem with this device is that it relies on additional components such and requires program to be "downloaded to the patient's computer 12 and transferred to the automated dosage console 10", thereby making it inconvenient and not easy to use on a daily basis, especially for the elderly that may not be computer savvy.

Other types of approaches include limited storage devices, such as in US patent U.S. Pat. No. 7,081,807B2. This device is compact; however, it has limited storage of only one type of medicine and involves manually setting the reminder each time the user opens. Additionally, the device requires the closure of the pill bottle cap where the electronic timer is located. The electronic timer comes with a factory predetermined time interval, is automatically activated, essentially making this similar to a wind-up alarm clock with no additional insight or programmability.

Additional devices, such as those depicted in US Patent application US20130134180A, allow setting of multiple reminders, however, the setting have to be manually configured and require cumbersome steps that are not useful for the sick or elderly.

Regardless of the device used from the above-mentioned examples, the patient is still in convenience to obtain water or other liquid at the time of consumption. For the lack of inconvenience alone, many get lazy or don't have the means and decide to delay or forgo their medication intake.

As such there is a need for a better solution that stores medications, provides convenience of having a liquid within for consumption, and provides an enhanced capability of managing pill/medication intake along with providing reminders for the intake.

SUMMARY OF THE INVENTION

A smart bottle used for storing liquids and medications is disclosed. The smart bottle includes electronics, memory, and a processor that causes alarms and reminders for its user to take their medications in a timely manner.

The bottle shaped smart bottle is essentially an electronic device with liquid and medication storage compartments. It includes speaker for providing audible alerts to the users as well as their caregivers. It also includes a microphone that can be used by the user or caregiver to provide instructions relating to the intake of medication or to assist patients that have hand or finger arthritis.

The bottle has a longitudinal and circular body with a cap that can be twisted on/off at its top. The top, or the cap, is a smart cap that carries core intelligence. It comprises a microprocessor, in-built real-time clock, speaker and lights for intuitive alarms, and a microphone for receiving a voice message or a voice command.

The microprocessor is communicatively coupled through an electronic circuit to a plurality of electronic components housed within the smart bottle. These include one or more alarms, microphones, displays, either a transmitter, GMS sim card, or Bluetooth for sending out information, and an antenna for wireless connectivity.

The longitudinal main body of the smart bottle is circular in shape and includes a chamber for storing liquids, such as water or other liquid. It also has compartments on its front and back side for storing a plurality of pills and medications.

The smart bottle is wirelessly connected to a server. It has the capability of connecting to a patient database to obtain all patient related information as well as medication information and hours of administration information. The smart bottle fetches prescription data automatically when linked to Pharmacy. At the time of intake for a pill, the smart bottle reminds user for respective dosages through use of lights or audio alarms. The smart bottle also sends alerts to a caregiver and stored adherence and compliance data to a server. To do so, the smart bottle uses the GSM sim card or Bluetooth to send alerts to mobile phone for reminding the user to take the medication or to send an alert to a caregiver.

The smart bottle also includes GSM and GPS modules. GPS mode allows the smart bottle to be located based on a GPS search. The GSM feature allows the user to make and receive calls from the smart bottle. A voice activation mode allows both dialing of phone numbers as well as instructions to operate various electronics ad modes of the smart bottle.

BRIEF DESCRIPTION OF THE DRAWINGS

The accompanying drawings are included to provide further understanding of the invention and constitute a part of the specification. The drawings listed below illustrate embodiments of the invention and, together with the description, serve to explain the principles of the invention, as disclosed by the claims and their equivalents.

DETAILED DESCRIPTION

Aspects of the invention are disclosed in the accompanying description. Alternative embodiments of the present invention and their equivalents are devised without parting from the spirit or scope of the present invention. It should be noted that like elements disclosed below are indicated by like reference numbers in the drawings. While the embodiments discussed below describe a smart bottle assembly device that allows storage of liquids and medications in chambers of the smart bottle, a smart cap that is wirelessly connected to a server for obtaining patient data, pill/medication data, and HOA, and the smart cap being equipped with a microprocessor that causes the operation of the microphone, speaker, alarms, transmitter, and antenna for the smart bottle, and a communications module that allows communications via the transmitter to mobile phone for providing alerts as well as for logging compliance and non-compliance data of the patient intake, the methods and embodiments listed are not so limited and equally applicable to other changes in sequence of steps, or use of other comparable embodiments.

Figure 1:
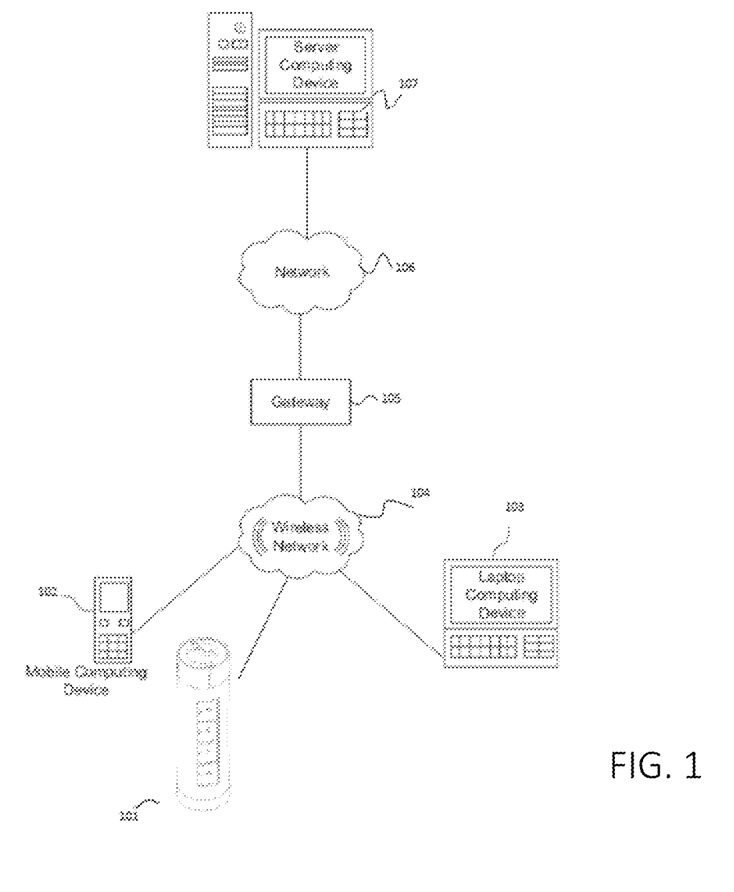
FIG. 1 depicts one embodiment of a system that is used in conjunction with the smart bottle assembly according to the disclosed embodiments.

FIG. 1 depicts one embodiment of a system that is used in conjunction with the smart bottle according to the disclosed embodiments. System 100 is used in connection with the smart bottle assembly 101. The system 100 includes one or more networks 104 and 106, such as a local area networks (LAN) and a wide area network (WAN) shown as network 106. The networks also store information related to electronic prescriptions submitted by a physician. The system 100 also includes wireless network 104 that allows devices in the network to wirelessly communicate with each other after pairing and/or other authorization between the devices.

Gateway 105 is configured to connect remote or different types of networks together, as well as client computing device 103 and server computing device 107.

Client computing device 103 may include any device capable of receiving and sending data over a network, such as wireless network 104. Device 102 may include portable devices such as cellular telephones, smart phones, radio frequency-enabled devices, personal digital assistants, hand-held computers, tablets, laptop computers, wearable computers and the like. The network is communicatively connected to the smart bottle assembly device 101 through the gateway and the wireless network 104. The device 102, a mobile computing device, can transmit prescription data to smart bottle assembly device 101, which is used in part to remind the end user for timely medicine dose intake.

Client computing device 103 may be web-enabled client devices that include a browser application configured to receive and to send web pages, web-based messages and the like. The browser application may be configured to receive and display graphic, text, multimedia, or the like, employing virtually any web-based language, including a wireless application protocol messages (WAP), or the like.

Client computing device 103 also may include at least one other client application that is configured to receive content from another computing device, including, without limit, server computing device 107. The client application may include a capability to provide and receive textual content, multimedia information, or the like. The client application may further provide information that identifies itself, including a type, capability, name, or the like. The server computing device 107 may also be part of the pharmacy where it can be used to access prescription generated by a physician, facility, or a clinic.

Client computing device 103 may also be configured to communicate a message, such as through email, short message service (SMS), multimedia message service (MMS), instant messaging (IM), which may include both video and audio messages to another computing device. Smart Bottle 101 (also a client computing device) may also receive audio and visual messages through the network or wireless network from an authorized user that can be audibly sounded from the smart bottle or can be displayed on a display that is on top of the smart cap.

The smart bottle may communicate with devices in the network using a wireless transmitter, such as a standard off-the shelf transmitter. Alternatively, the smart bottle may communicate to other mobile devices over the air without Bluetooth. Other methods of sending and receiving signals and messages to internet capable devices are also contemplated. For example, the wireless transmitter along with an antenna may be used to send an alert to a caregiver's mobile phone. It may also include an RFID tag that can store information related to the patient, pills or medications, and hours of administration.

Figure 2:
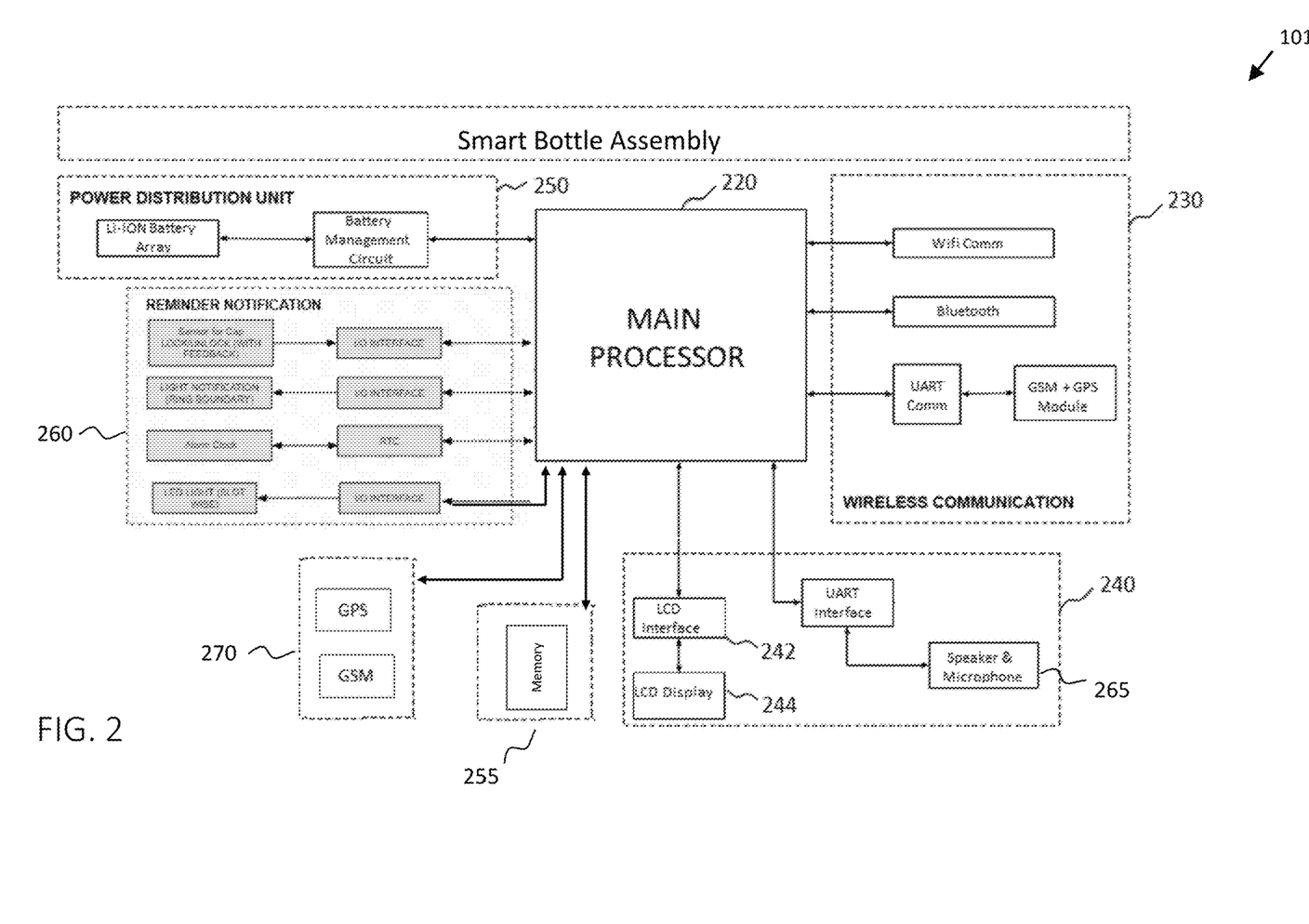
FIG. 2 illustrates a block diagram of some of the hardware components of the smart bottle assembly according to the disclosed embodiments.

FIG. 2 illustrates a block diagram of some of the hardware components of the smart bottle according to the disclosed embodiments. The smart bottle assembly 101 uses a main processor (microprocessor) 220 to configure and process and command hardware components within the smart bottle assembly 101 to function in a desired manner. Main processor 220 also utilizes the hardware components and instructs them to wirelessly connect to a mobile application located on a mobile device and executes functionality to connect to a server computer's database to obtain patient details, such as prescriptions, medications, physician notes, medical history and/or hours of administration (HOA) data.

As mentioned above, the smart bottle assembly 101 connects to electronic devices and communicates using the hardware components to perform the functions needed for reminding the user to take their medications and alerting a caregiver if non-compliance is detected. The functions further include providing audible and visual alerts before the time to take the medication, alerts at the time of administration, post alerts after the time to take the medication has passed, and notification to the caregiver or authorized person of the non-compliance. The audible and visual alerts are given on the smart bottle assembly 101 while the alerts to the mobile devices use the mobile device's speaker and sounds.

The main processor 220 is coupled to memory module 255. Upon retrieval of patient, medication, prescription, or HOA data from a server's database, the processor stores that data in the smart bottle assembly's memory 255.

The processor 220 is also connected to the wireless communication module 230, display and communication hardware 240, which includes LCD interface 242, LCD display 244, speaker and microphone, power distribution unit 250, reminder notification module 260, GPS and GSM Module 270.

The main processor 220 is also connected through digital circuitry to a battery management circuit (not shown). The processor utilizes the battery's capacity by preventing localized under-charging or over-charging. Although the battery act is connected to various hardware components, such as led lights, speaker, microphone, LED display, to provide power for their operation, in the case of LED lights, they are connected to the main processor via I/O interface. The LED lights get triggered by the main processor 220, which results in the LED lights glowing at an HOA.RTC module (real time clock) is attached with the main processor that helps to keep track of current time and date.

The WIFI communication module 230 connected to the main processor 220 allows hosting of an application or offloading all WIFI networking functions from another application processor. In one embodiment, a Bluetooth 4.1 and BLE is connected with the main processor 220. This Bluetooth, which is a low energy Bluetooth uses the same 2.4 GHz radio frequencies as classic Bluetooth and allows dual-mode devices to share a single radio antenna.

The GSM and GPS modules 270 are connected to main processor 220 through UART communication (Universal asynchronous receiver-transmitter) for cellular network connection and location-tracking respectively.

The LCD display 244 is connected to the main processor 220 through the LCD interface 242. The LCD display is used for showing messages, alerts, time, or medication related information to its users.

The speaker and microphone 265 are also connected to the main processor 220 through digital circuitry. The speaker is capable of producing the audio output that can be an alarm for the end user. The microphone is connected with the main processor via UART communication. The microphone captures audio by converting sound waves into an electrical signal. This signal can be amplified as an analog signal or may be converted to a digital signal, which can be processed by the main processor 220 or another digital audio device which is connected to the cloud.

The main processor 220 is adapted to execute stored instructions, the memory module 255 to provide memory space for operations of said instructions during operation. The processor 220 can be a single-core processor, multi-core processor, computing cluster, or any number of other configurations. The memory 255 can include random access memory (RAM), read only memory, flash memory, or any other suitable memory systems. The memory module may store applications 1 through N that may be used to store patient, medication, and HOA related data and the stored information can be used to remind the users of the smart bottle assembly 101 to timely intake the medication.

It is to be understood that the block diagram of FIG. 2 is not intended to indicate that the smart bottle assembly 101 is to include all of the components shown in FIG. 2. Rather, the smart bottle assembly 101 can include fewer or additional components not illustrated in FIG. 2 (e.g., additional memory components, embedded controllers, modules, additional network interfaces, etc.).

Figure 3A:
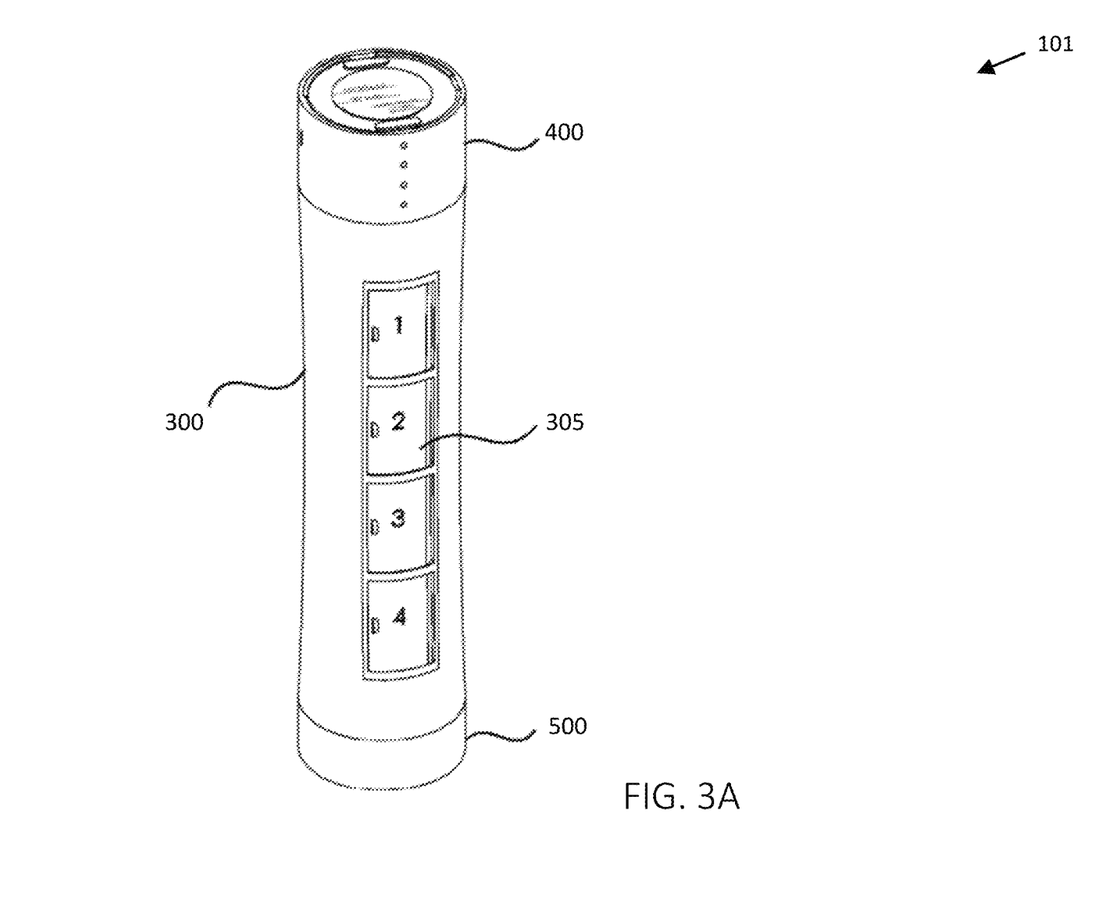
FIG. 3A is an isometric view of the front face of the smart bottle assembly according to the disclosed embodiments.

FIG. 3A is an isometric view of the front face of the smart bottle assembly according to the disclosed embodiments. This embodiment depicts the smart bottle assembly 101 in its closed position. The smart bottle assembly 101 functions as part of the networked system shown in FIG. 1 and uses the hardware architecture shown in FIG. 2.

The smart bottle assembly 101 is used for multiple purposes. These include acting as a medicine intake reminder for reminding its user to timely intake a medication in accordance with its hours of administration (HOA) as prescribed. HOA of administration or HOA are times of the day or week when a medication is to be administered. For example, the HOA can be on a specific day of the week, every day, or multiple times a day, or only at a certain time of day that is before or after a meal. HOA is typically customized for each patient based on their medical condition.

The smart bottle assembly 101 also functions to provide information to the user/patient on details of the medication, its side effects, its expiration dates, as well as the time window within which it should be taken. The information assists the user to ensure the medication is properly administered to avoid any medical issues, manage risks, and prevent untimely intake.

Yet another function of the smart bottle assembly 101 is to allow storage of liquids and medications in one container thereby making it convenient for its user to intake a medication along with liquid as desired. To do so, the smart bottle assembly 101 contains separate chambers/compartments for storing liquid and a plurality of medications.

Another function of smart bottle assembly 101 is to send an alert to either its user, caregiver, of both to remind them of timely medication intake as well as send second and consequent reminders either before or after the HOA. The alerts are sent to mobile devices that are authorized and communicatively connected with the smart bottle assembly 101 over network of FIG. 1.

Another function of the smart bottle assembly 101 is to allow voice activation by its user to activate electronic features of the smart bottle assembly 101 or make a phone call using its GSM feature in the GPS+GSM module 270. Similar to keys, since household items are often misplaced, smart bottle assembly 101 also allows use of its GPS feature, from its GPS+GSM module 270, to locate it within the house or outside.

Yet another function of the smart bottle assembly 101 is to display medication related information, messages, or other reminders, on its display 244.

These additional features and functionality, that will be discussed through this application is achieved through the three-piece structure that forms the assembly for the smart bottle assembly 101. These three pieces include, a central or main housing 300, a smart cap 400, and a vital doses casket 500.

Figure 3B:
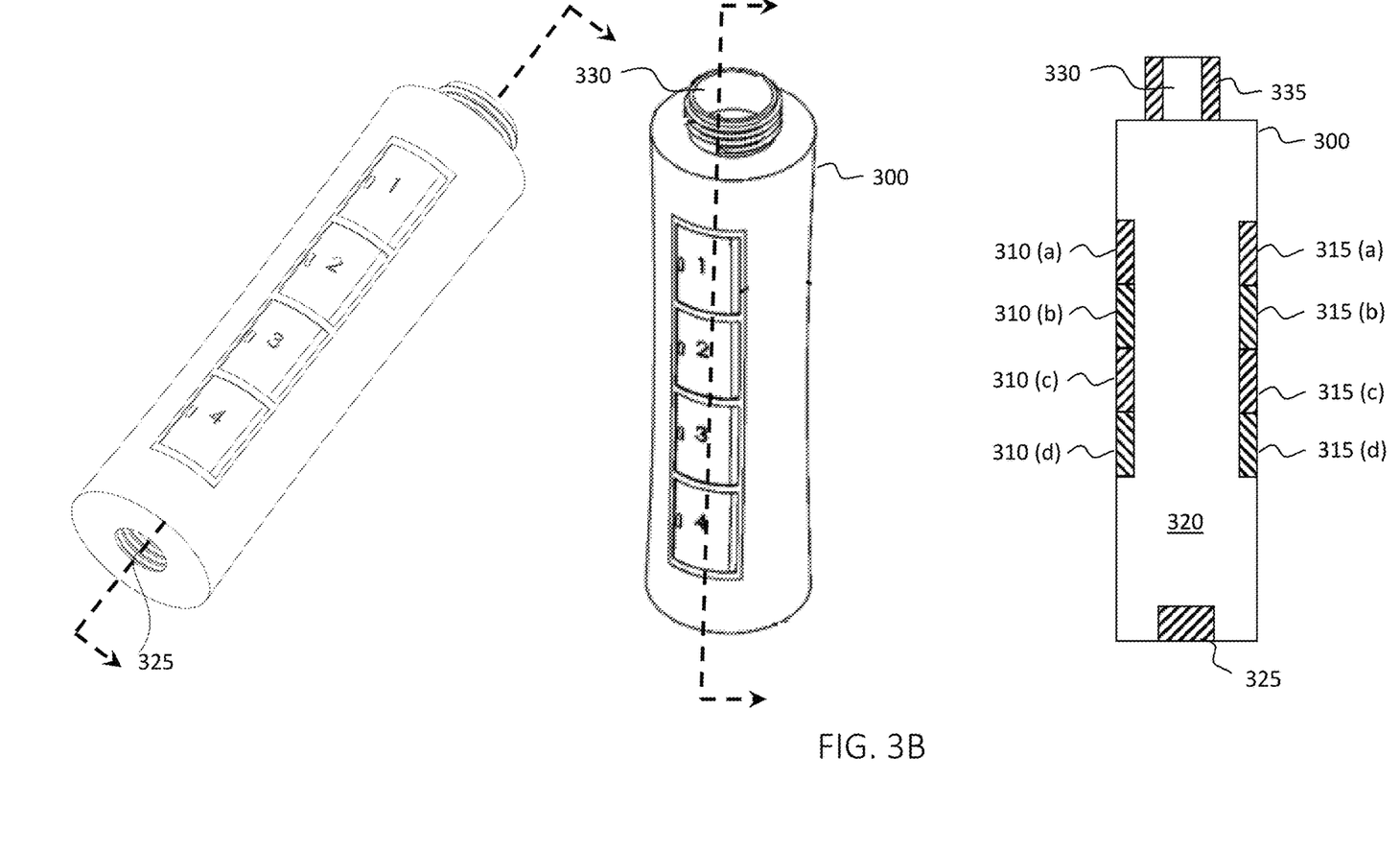
FIG. 3B depicts a cross-sectional view of the main housing of smart bottle assembly according to the disclosed embodiments.

FIG. 3B depicts a cross-sectional view of the main housing of smart bottle assembly according to the disclosed embodiments. The main housing 300, includes a plurality of daily doses casket, also referred to as chambers or compartments, 310(*a*)-310 (*d*) on the front face of the main housing and 315(*a*)-315 (*d*) on the rear face of the smart housing. Since the main housing is circular, front and back are interchangeable and they are described as such in this embodiment to provide a frame of reference.

The daily doses casket allows its user to store medicine dosages. It comprises of different compartments for each specified dose and or each specified medication. It helps end user to take medication with convenience.

In one embodiment, the daily doses caskets comprise of two days dosage capacity. Alternatively, it can be varied to any suitable number of doses as required/desired. The daily doses caskets can be digitally locked, child proofed, and automated with a timer to open the lock at the HOA. When Daily dose caskets, i.e. 310(*a*)-310 (*d*) on the front face of the main housing and 315(*a*)-315 (*d*) on the rear face, are equipped with child lock (not shown), it receives input for dose taken as soon as the user opens it. Other means of getting input for "Dose taken" can be used.

A plurality of LED's is linked to daily doses caskets identifying each casket separately from another to make it visibly convenient to gather the dose from the illuminated compartment at the HOA.

A flask 320 is at the center of the main housing 300. The flask has retaining walls to prevent the liquid from escaping. In one embodiment, the flask 320 includes either a thermal layer, coating, or protective layer to retain the fluid temperature within the flask for an elongated time period. Inside the main housing, there is a wall separating the flask and the daily doses caskets thereby preventing any liquid to enter the daily doses caskets and isolates both the medications and the liquids separately. Additional layers, such as food grade material tritan is used to protect the end user from any disease and contamination.

The spout 330 also includes its threaded retaining wall 335. The spout is narrow which provides for easy drinking of the liquid stored in the flask 320.

At the bottom of the main housing 320, a threaded hole 325, which is a hollow cavity having a female threaded receiving section, allows for insertion of the vital doses casket 500.

Referring back to FIG. 3A, the smart bottle assembly 101 includes a smart cap 400. The smart cap 200 refers to the part of the apparatus that comprises of entire electronics required for functioning of smart bottle assembly 101 as well as connecting to devices outside the smart bottle assembly 101 for receiving or sending information.

The smart cap 400 includes a matably threaded section that mates with the threaded receiving end of the spout and then mated fits onto the main housing thereby preventing ant debris from entering the flask 320.

The smart cap 400 also includes a display for easy Human-machine interface.

At the bottom of the smart bottle assembly 101, is the vital dose casket 500. It has a male threaded section that can be inserted at the bottom of the main housing for mating and connecting with the internal thread of the flask. Once mated, the vital dose casket 500 is locked in with the main housing 300.

Figure 3C:
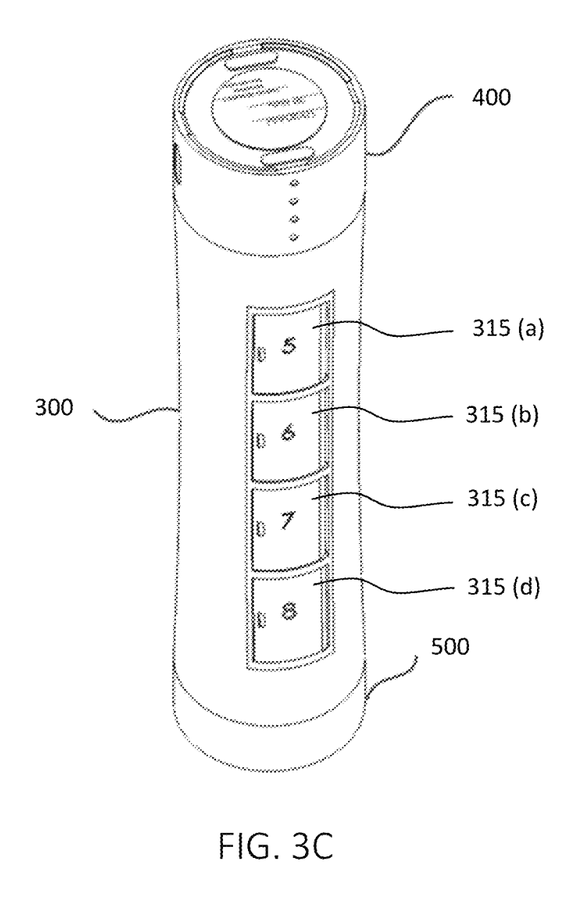
FIG. 3C is an isometric view of the rear face of the smart bottle assembly according to the disclosed embodiments.

FIG. 3C is an isometric view of the rear face of the smart bottle assembly according to the disclosed embodiments. As mentioned earlier, the front and rear are interchangeable. The rear view also depicts a plurality of daily dose caskets, i.e. 315 (*a*)-315 (*d*). Although a total of two sides having 8 daily dose caskets in a series of 4 on each side are depicted, other contemplations, such as having a $3^{rd}$ or a 4rth side adjacent to the two sides, or having smaller daily dose caskets to accommodate more than 4 in a row are also included.

Figure 4:
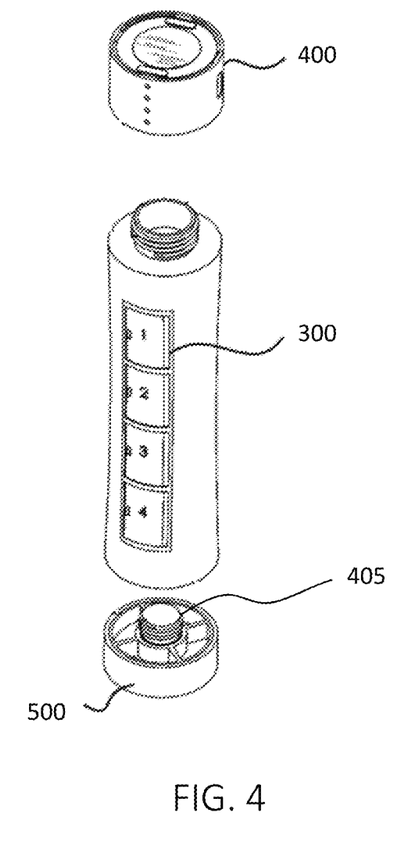
FIG. 4 is an exploded isometric view of the smart bottle assembly according to the disclosed embodiments.

FIG. 4 is an exploded isometric view of the smart bottle assembly according to the disclosed embodiments. The three-piece assembly makes up the smart bottle assembly 101. Although the electronics, such as processor and other electrical components are in the smart cap 400, it is contemplated that the electronics can be placed in either the main housing 300 or the vital dose casket 500.

The three-piece assembly allows mating and detaching of each piece to another by using their respective male-female threaded fasteners.

In one embodiment, certain electronics and lighting are placed in the main housing 300 and vital dose casket 500 while the main processor 220 and the battery are stored in the smart cap 400. The main housing 300 and vital dose casket 500 may include part of the digital circuit, which form the connection between the smart cap 400 and the main housing 300 and vital dose casket 500 upon attachment of the pieces to each other thereby completing the digital circuit that carries the current and power to other electronic components placed in the main housing 300 and vital dose casket 500. For example, the main housing may include some lighting or display that can be illuminated or displayed upon completion of the circuit when the main housing 300 comes in contact with the smart cap 400. Alternatively, they may also receive power and complete the circuit through wireless means.

The vital doses casket 500 includes external threads 405 that smoothly merges with internal threads 325 of the main housing 300 upon rotation. The vital dose casket has its own compartments for storing medications. The vital dose casket 500 can be used for storing take-as-needed medicines, or medication that are not part of the required regimen.

Figure 5:
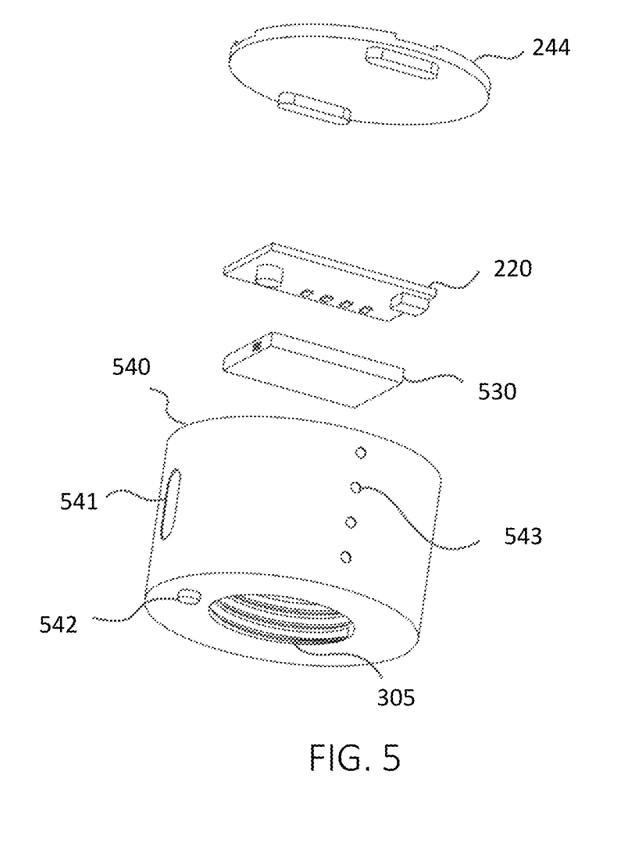
FIG. 5 is an exploded view of the smart cap that is part of the smart bottle assembly according to the disclosed embodiments.
Figure 6:
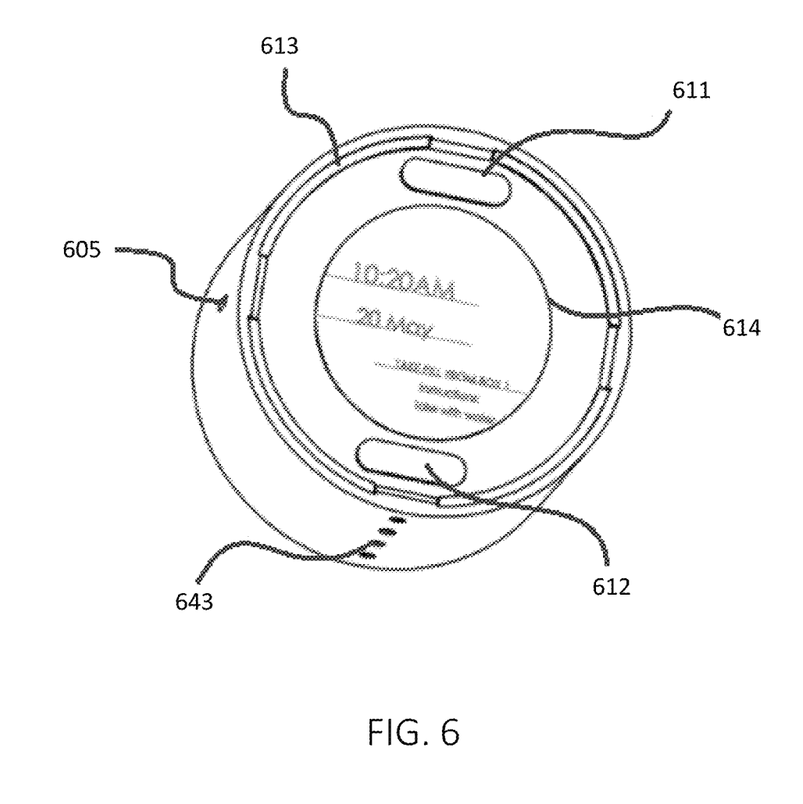
FIG. 6 is a top perspective of the smart cap that is part of the smart bottle assembly according to the disclosed embodiments.

FIG. 5 is an exploded view of the smart cap that is part of the smart bottle assembly according to the disclosed embodiments. FIG. 6 is a top perspective of the smart cap that is part of the smart bottle assembly according to the disclosed embodiments. Both figures depict the smart cap 400 and they will be discussed together below.

The smart cap is used both as a cap for the flask of the main housing as well as core electronics module that provides processing and battery power for the electronic hardware in the smart bottle assembly 101. To do so, the smart cap 400 includes the main processor 220 communicatively coupled to the display panel 244, and battery 530 all housed within the body 540 of the smart cap. The smart cap 400 includes internal threads 305 that wind on external threads of main housing 300 to attach. The engagement of threads also prevents any debris from outside from entering the flask thereby achieving an airtight or near air tight arrangement.

The display panel 244 includes expansion capability to add a microphone 611, and or a speaker 612. It also includes capability to add an LED lamp ring 613 along with centered visual interface 614.

Microphone 611, as mentioned above, is used for multiple purposes. In one embodiment, it is used for recording a message, reminder, or a voice note that can be stored in the memory 255 of the smart bottle assembly 101 and played back at an appropriate time or at the HOA. In another embodiment, the microphone is used as a means for voice activation processing to receive an instruction from the user and then allow the main processor 210 to process that information for executing appropriate commands, such as for example, to make a phone call, illuminate a certain medical doses casket, or to unlock it, providing the user voice activation to run the smart bottle independent of a mobile application. Alternatively, an authorized mobile application may be communicatively coupled to the smart cap 400 for executing its functionality when a voice command is not spoken into the microphone.

The speaker 612 is used to listen to audio reminders for scheduled dosages. It can also be used to hear the voice of loved ones as reminder notification. The speaker and microphone can be independently activated through voice activation or be coupled with a mobile application. For e.g. If the user has upcoming dose scheduled for 1:00 pm, then the audio alert will be given at a predetermined time that can be selected using the mobile application or provided to the smart bottle assembly using voice activation and speaking into the microphone. Likewise, other clock-like features such as snooze can also be activated.

The smart cap 400 is also used for compliance. This compliance refers to timely intake of the medication. In one embodiment, the user is prompted a Yes/No response. If user does not press or respond with a "Yes" to Dose taken, then an alert is set off at the smart bottle. The alert may also be sent to a mobile device of the user and/or an authorized caregiver.

Other methods to electronically monitor the timely intake are also contemplated. For example, the user cannot simple spoof or fool the application by responding affirmatively to dose taken when in fact the dose has not been retrieved from the compartments of the smart bottle main housing. An electronic detection is performed to determine if the correct compartment was opened and if medication was taken out. The compliance or lack thereof is recorded to medical adherence history for each patient and stored in the memory of the smart bottle as well as sent to a database on a server for recording.

The visual interface 614 displays instructions, parameters, and messages to the user. Some of the displayed information can include time, date, battery percentage, instructions on how to take medicine, medical adherence bar, scheduled alert for next dose, language selection, a phone contact list, or voice to text conversion of what the user has spoken into the microphone.

The visual interface can also guide its user on how to navigate through the functionality of the smart bottle assembly 101 by displaying instructional information. Using the visual interface, the user can also select different modes of notification, e.g. email, text, or call for caretaker/guardian. The user can also ask for one's medical adherence history to check about present state of health.

The smart cap includes a GPS locator that also automatically selects time zone of its location and changes the time zone upon travel into another zone.

User gets refill notification, from where itself the order can be placed and the user can also snooze the reminder for future time-period according to one's convenience.

The main processor 220 is connected to the battery 230, which may be a lithium-ion battery, via battery management and monitoring system (BMMS) which helps to maximize the battery's capacity and to prevent localized under-charging or over-charging via charging slot (605). The Battery management and monitoring system (BMMS) encompasses not only the monitoring and protection of the battery but also method for keeping it ready to deliver full power when called upon and methods for prolonging its life. This includes everything from controlling the charging regime to planned maintenance.

The main processor 220 is also communicatively connected the GSM+GPS module 270. The module provides communication and data connectivity over air for internet and phone calls. The Wifi module allows hosting an application or offloading all Wifi networking functions from another application processor. The RTC module (real time clock) helps to keep track of current time and date, Bluetooth 4.1 & BLE is low energy Bluetooth uses the same 2.4 GHz radio frequencies as classic Bluetooth, which allows dual-mode devices to share a single radio antenna.

The bottom portion of the smart cap 400 includes an ON/OFF button 541. This button is used for switching on/off the electronics of the smart bottle assembly 101.

The smart cap 400 also includes pressure Sensor 542. These sensors detect the opening and closing of cap to track the intake of medication, illuminating of the LED indication strip 643 to indicate the opening of a slot of daily dose caskets 310(a)-310 (d) on the front face of the main housing and 315(a)-315 (d) on the rear face of the smart housing.

The ON/OFF switch is an electrical device that is used to break or make an electrical circuit manually or automatically. Various electrical or electronic circuits use switches to control or trigger the circuit. In one instance, the ON/OFF button 541 is used to trigger the circuit of smart bottle assembly 101. Pressure sensor 542 is used to get input signal for patient to take its dosage on correct time. Considering daily dose caskets 310 (a)-(d) and 315 (a)-(d) and the flask to hold liquids is part of one assembly, if Smart cap 400 is placed upon the main housing 300, it senses a pressure that is caused by compression by the attachment. The detachment also releases the pressure thereby signifying that the user may have opened the flask to drink water or liquid while taking a medication, thereby adding another laying or verifying compliance.

As mentioned above, the smart bottle uses Pressure sensor 542 in one embodiment to determine compliance. However, the smart bottle is capable of distinguishing between the opening of the cap during an HOA, which would imply that the user has consumed liquid from the flask while taking their medication, and opening of the flask lid outside of the HOA when the user is simply using the flask as a water bottle. Its able to correlate as such by correlating with HOA as well as determining if any one of the dose caskets were opened within the same time frame. For example, if pressure sensor sense opening of the cap, then it receives data from another sensor in the smart bottle that monitors dose casket opening, and it also receives data from HOA to determine if it was time for a medication intake, and triangulating these three points of date determines a compliance.

In another embodiment, if Smart cap 400 is open to atmosphere, it senses Atmospheric pressure of 1.013 bar. This acts as yet another compliance verification to verify that the user opened the flask for drinking a liquid along with taking the medication. Compliance verification by other methods is also contemplated.

A plurality of LED strips is placed on a plurality of sides of the smart cap 400. For example, four LED indication strip 543 are placed on two sides of smart cap 400 and illuminated at HOA to guide the user in retrieving the medications from the correct compartment. Distinct colored LEDs for separate compartments are also contemplated.

Figure 7:
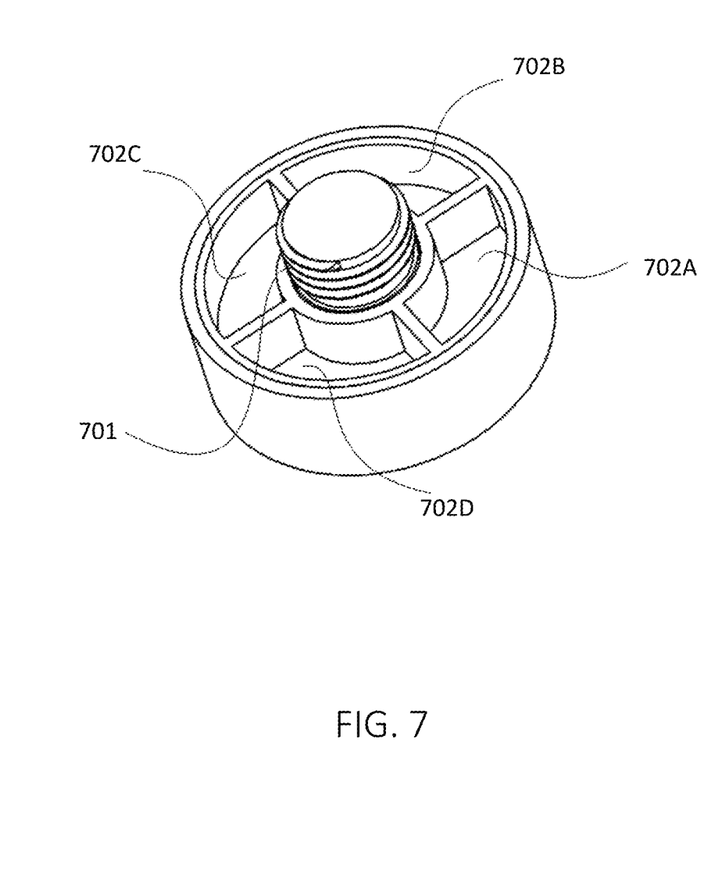
FIG. 7 is a top perspective view of the vital dose casket with open slots according to the disclosed embodiments.

FIG. 7 is a top perspective view of the vital dose casket with open slots according to the disclosed embodiments. The vital doses casket 500 is used for storing medications that are not prescribed or not part of a daily regimen that is to timely taken according to HOA. Those medications are placed in compartment 310(a)-310 (d) on the front face of the main housing and 315(a)-315 (d) on the rear face of the smart housing since they need monitoring and checked for compliance. The medications stored in the vital doses casket 500 on the other hand do not need monitoring and can be taken by the user at desired or needed times, such as ibuprofen (such as Advil or Tylenol) for headache or pain.

The vital doses casket 500 includes a threaded protrusion 701 and a plurality of chambers 702A-702D. The extruded flange of the threaded protrusion 701 fits into hole 325 of the main housing 300 for attachment.

The plurality of chambers 702A-702D is used for storing medications. Each chamber has a lid that can open up to 120 degrees for ease of access to medicines. A hinged lid mechanism shown allows closing and opening of the door that rotates about the axis of extruded flange 701. The lid may be locked or have a push mechanism is opened upon applying pressure. Other mechanisms to secure the medication in its place without having is fall are also contemplated.

Figure 8:
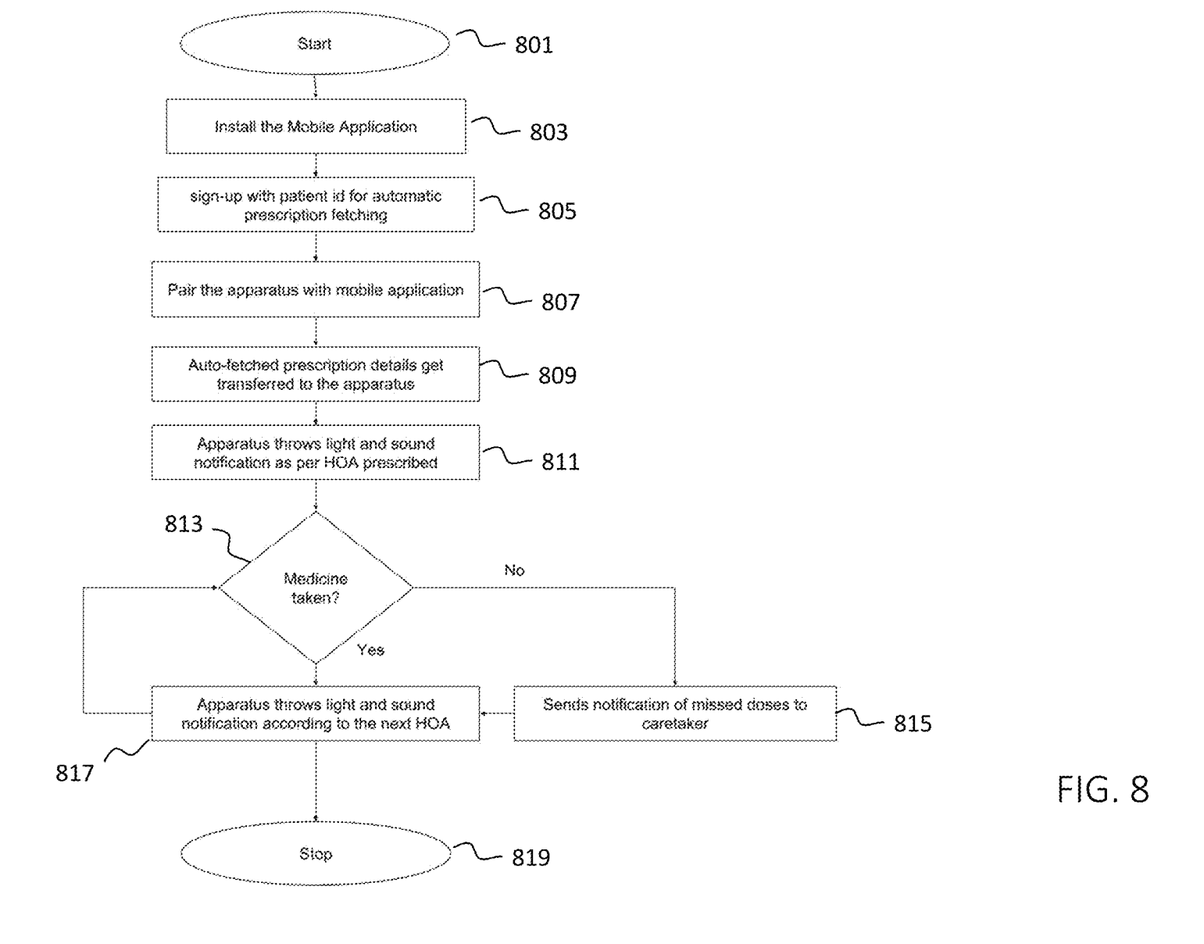
FIG. 8 is a flowchart depicting one exemplary cycle of operation for the smart bottle assembly according to the disclosed embodiments.

FIG. 8 is a flowchart depicting one exemplary cycle of operation for the smart bottle assembly according to the disclosed embodiments.

At step 801, the process is started and at step 803 a mobile application is installed for the smart bottle assembly 101 in Mobile Computing Device 102. Upon installation, at Step 805, the patient registers with a patient id for automatic prescription fetching. The registration authorizes and acts as patient consent to obtain patient specific data. The prescription includes the name/details of the medicines present in the doses with hours of administration and the instructions at the time of taking medicines, for example if the prescription has an hour of administration twice a day "morning 9 AM and evening 6 PM" and the instruction such as "To be taken with Water".

At Step 807, the mobile application is paired with the smart bottle assembly 101 using a wireless network 104.

At Step 809, once the paired, auto-fetched prescription details get transferred to the smart bottle assembly 101 and are then stored in memory 255. To indicate pairing is completed, the LEDs on the smart bottle assembly 101 may be illuminated.

At Step 811, smart bottle assembly 101 illuminates certain LEDs and produces certain sounds at HIA to guide and associate the user with the correct medication to be timely taken. As mentioned earlier, the illumination and sounds are part of the alerts provided to the user and they can be set at a predetermined time, such as 10 minutes before HOA, or let the mobile application select from preset settings. The changes in colors of LED and intensity of sound can occur as time for taking the medication gets closer to HOA as well as when the time has lapsed. Additionally, the mobile application may also send alerts to a caregiver's mobile device upon noncompliance.

At Step 813, a determination is made whether the medication has been taken. The determination can be user provided as well as verified through electronic means to determine a certain medication storage compartment was opened, if the flask was opened etc.

At Step 815, a notification is sent to a caregiver upon noncompliance. Both compliance and non-compliance are then recorded into the memory of the smart bottle assembly as well as a database on a server.

At Step 817, the smart bottle assembly 101 moves to the next HOA and repeats the process, determination and notification steps 811, 813, and 815. At step 819, once all the medications have been taken, the process ends.

It will be apparent to those skilled in the art that various modifications and variations can be made in the smart bottle assembly and associated methods without departing from the spirit or scope of the invention. Thus, it is intended that the present invention covers the modifications and variations of the embodiments disclosed above provided that the modifications and variations come within the scope of any claims and their equivalents.

What is claimed is:

1. A portable smart bottle used for storing liquids and medications and reminding its users or patients to timely administer the stored medications, the smart bottle comprising:
    a main housing used for storing the liquids and medications, wherein the main housing is longitudinal and has a cylindrical shaped body, wherein the main housing has an upper and a lower end, wherein the main housing includes an inside chamber, a front facing side, and a longitudinal side, wherein the main housing further comprises
        an enclosed liquid chamber that is used for storing liquids, wherein the liquid chamber is centrally located inside the cylindrical shaped body and runs longitudinally from the lower to upper end,
        a thermal layer surrounding the liquid chamber such that the inside chamber is insulated as well as enclosed to prevent any liquid from leaking to the outside of the liquid chamber,
        a plurality of medication storing compartments located outside the thermal layer, wherein a first set of medication storing compartments located on the front facing side of the main housing and the second set of medication storing compartments located directly opposite 180 degrees from the first set of medication storing compartments, wherein the plurality of medication storing compartments are placed along the longitudinal side on the main housing;
        the main housing having an upper dispensing end, wherein the upper dispensing end has a shoulder extending upwardly and inwardly from the upper end of the main housing, and the upper dispensing end having a dispensing spout extending upwardly from the shoulder, and
        the lower end of the main housing that has a circular threaded opening on its bottom to allow for insertion;
    a lower cap having male side mating threads for insertion into the circular threaded opening at the bottom of the main housing;
    a smart cap having a circular housing, wherein a bottom of the smart cap housing includes a threaded section that fits on the spout of the upper dispensing end of the main housing to securely fasten the smart cap with the main housing thereby preventing liquid inside the liquid chamber from escaping when fastened;
    a microprocessor housed within the smart cap housing; and
    a plurality of electronic components housed within the smart cap housing, wherein the electronic components include a speaker, a microphone, a digital display, a transmitter, an antenna, and memory, wherein an electronic circuit connects the microprocessor to the electronic components to perform the function of doing a medication inventory for medications housed in the smart bottle, patient data retrieval and storage, medication data retrieval and storage into the memory, prescription and hours of administration data retrieval and storage into its memory, and alerting the user of the smart bottle for timely intake of the medications housed in the smart bottle.

2. The portable smart bottle of claim 1, wherein the smart cap further includes an in-built real-time clock, a Wifi module, and lights.

3. The portable smart bottle of claim 1, wherein the transmitter wirelessly connects the smart bottle to a mobile application that is downloaded on a mobile device, wherein the mobile application is used for setting preferences, directing functionality of the electronic components, and setting alerts and reminders in the smart bottle.

4. The portable smart bottle of claim 3, wherein the mobile application performs the steps of:
selecting one or more authorized users for receiving an alert, wherein the alert is a reminder that it is time to take a medication that is housed in the smart bottle, wherein the timing of the alert is obtained in accordance with a prescribed hour of administration that has been prescribed by a physician for a patient that is to take the medication; and
recording compliance or non-compliance of intake of the medications, wherein such recording captures data that shows timely intake of the medication, delayed intake of the medication, and non-compliance or not taking of the medication.

5. The portable smart bottle of claim 3, wherein the mobile application performs the steps of:
receiving prescription data from a database that houses patient information, wherein the prescription data is obtained from the database by querying a unique ID that is associated with a specific patient;
extracting the information contained in the prescription and parsing it to obtain hours of administration (HOA), medication details, and patient details; and
automatically setting up alerts that correspond with the HOA that remind the patient to timely take the medication at the HOA.

6. The portable smart bottle of claim 5, wherein the alert is set at a predetermined interval before the HOA.

7. The portable smart bottle of claim 5, wherein a time of the alert is customized and entered through the mobile application.

8. The portable smart bottle of claim 5, wherein the microprocessor causes the speaker in the smart bottle to sound an audible alarm or an audible pre-recorded message at a time of the alert.

9. The portable smart bottle of claim 5, wherein the microprocessor causes an LED located on the smart cap to illuminate at a time of the alert.

10. The portable smart bottle of claim 9, wherein the LED emits a colored light.

11. The portable smart bottle of claim 3, further comprising a GPS module, wherein the mobile application activates the GPS module to track and locate the smart bottle.

12. The portable smart bottle of claim 3, wherein the plurality of medication storing compartments are automatically locked by the smart bottle and only the compartment that contains a medication that is to be taken opens up at or before the medication's hour of administration.

13. The portable smart bottle of claim 12, wherein the transmitter wirelessly connects the smart bottle to the mobile application that is downloaded on the mobile device, wherein the mobile application obtains the hour of administration from a database stored on a computer, and uses the hour of administration to determine which medication compartment to lock and unlock at the hour of administration, thereby eliminating accidental consumption of a medication that is stored in a different medication storing compartment.

14. The portable smart bottle of claim 1, further comprising a GSM module, wherein the GSM module allows the user to make a voice call from the smart bottle to a phone number, wherein the microphone is used for making the voice call.

15. The portable smart bottle of claim 14, further comprising a voice activation controller, wherein the voice activation controller is communicatively coupled to the microphone of the smart bottle, wherein the voice activation controller
receives instructions that are spoken into the microphone by the user, and converts the instructions thereby activating the GSM module to dial either a prerecorded phone number or a new phone number spoken into the microphone by the user.

16. The portable smart bottle of claim 1, further comprising a voice activation controller, wherein the voice activation controller is communicatively coupled to the microphone of the smart bottle, wherein the voice activation controller
receives instructions that are spoken into the microphone by the user, and converts the instructions to activate an electronic feature of the smart bottle.

17. The portable smart bottle of claim 16, wherein the electronic feature activated through voice activation is the internal clock to set a timer for reminding to take a medication.

18. The portable smart bottle of claim 1, wherein the liquid housed in the enclosed liquid chamber is water.

19. The portable smart bottle of claim 1, wherein the thermal layer retains the temperature of both hot and cold liquids.

* * * * *